United States Patent [19]

Takaku et al.

[11] 4,342,828

[45] Aug. 3, 1982

[54] METHOD FOR PRODUCING SUBSTANCE CAPABLE OF STIMULATING DIFFERENTIATION AND PROLIFERATION OF HUMAN GRANULOPOIETIC STEM CELLS

[75] Inventors: Fumimaro Takaku, Utsunomiya; Katsuhiro Ogasa, Yokohama; Morio Kuboyama; Nobuya Yanai, both of Tokyo; Muneo Yamada, Kodaira; Yoshiteru Watanabe, Tokyo, all of Japan

[73] Assignees: Morinaga Milk Industry Co., Ltd., Tokyo; The Green Cross Corp., Osaka, both of Japan

[21] Appl. No.: 169,107

[22] Filed: Jul. 15, 1980

[30] Foreign Application Priority Data

Jul. 20, 1979 [JP] Japan .................................. 54-92355
May 15, 1980 [JP] Japan .................................. 55-64625

[51] Int. Cl.$^3$ ........................ C12N 5/00; C12P 19/26
[52] U.S. Cl. ....................................... 435/41; 435/68; 435/240; 424/99; 424/101; 424/115; 424/177
[58] Field of Search ....................... 435/41, 240, 68, 2; 424/99, 101, 115, 177

[56] References Cited

U.S. PATENT DOCUMENTS 4,135,975  1/1979  Lichtman et al. .................. 435/240
4,275,056  6/1981  Takaku et al. ........................ 424/99

OTHER PUBLICATIONS

Motoyoshi et al., *Chemical Abstracts*, 89:142164t, 213 (1978).
Stanley et al., *Federation Proceedings*, 34(13), 2272–2278 (1975).
Price et al., *Biochemical Journal*, 148, 209–217 (1975).
Shah et al., *Blood*, 50, 811–821 (1977).
Motoyoshi et al., *Chemical Abstracts*, 90:1931Z, 192 (1979).

*Primary Examiner*—Esther M. Kepplinger
*Attorney, Agent, or Firm*—Cushman, Darby & Cushman

[57] ABSTRACT

A colony stimulating factor effective in treating human granulocytopenia is produced by cultivating monocytes and macrophages isolated from the human peripheral blood in a synthetic medium for tissue culture containing a glycoprotein isolated from human urine and capable of stimulating the formation of human granulocytes or mouse macrophages and granulocytes.

10 Claims, No Drawings

METHOD FOR PRODUCING SUBSTANCE CAPABLE OF STIMULATING DIFFERENTIATION AND PROLIFERATION OF HUMAN GRANULOPOIETIC STEM CELLS

This invention relates to a curative for human granulocytopenia and, more particularly, to a method for producing a substance which directly acts on human granulopoietic stem cells (hereinafter referred to simply as stem cells), thereby stimulating the proliferation and differentiation of said cells [hereinafter such a substance is referred to as CSF (colony stimulating factor)].

It has been widely known that CSF plays a key role in the granulopoiesis and monocyte (cells yet to grow to macrophages) and/or macrophage formation in vivo and because CSF in the living human body acts on the stem cells, which are the mother cells for the said granulocyte, monocyte and macrophage, to induce their proliferation and differentiation [Metcalf, D., Experimental Haematology, Vol. 1, 185–201 (1973)]. The CSF having such a biological activity has been expected to become useful as a medicament for treating granulocytopenia [Fumimaro Takaku, Igaku no Ayumi (Progress in Medical Science), Vol. 95, No. 2, 41–50 (1975)]. The actual use of CSF as a medicinal agent, however, has not yet been realized for the reasons such that the mechanism of formation of granulocytes, monocytes and macrophages in vivo is complicated, that there still remained unknown part in the behavior of CSF in said mechanism, and that it was difficult to produce large quantities of CSF of a pharmacologically acceptable quality.

As for the use of CSF as a diagnostic reagent, it was known that the measurement of the number of CSF-responsive cells in bone marrow cells is of great significance for the prognosis on a patient suffering from myelogenous leukemia (Nakao and Takaku, Ed.: "Proliferation and Differentiation of Blood Cells—Fundumental and Clinical aspects—", p. 29, Published by Kagaku Hyoronsha Co., Japan, 1975) and CSF is useful as a reagent (reference stimulator) for this purpose. However, similarly to the case of above-noted pharmaceutical use, the use of CSF in diagnosis has not yet been put into practice because of the difficulty in producing large quantities of CSF having a quality sufficient enough for the diagnostic use.

For the preparation of CSF which acts directly on the stem cells, there have been known those methods which involve cultivation of white blood cells of the human peripheral blood (Price, G. B. et al., Biochemical Journal, Vol. 148, 209–217 (1975)], human placental cells [Burges, A. W. et al., Blood, Vol. 49, No. 4, 573–583 (1977)] or a certain kind of cancer cells called CSF-producing tumor (Nakaaki Osawa et al., Acta Hematologica Japonica, Vol. 42, No. 2, 237 (1979)]. Among these methods, those which may possibly produce CSF suitable for pharmaceutical use are the former two. However, the conventional methods utilizing the said cells are experimental methods for the preparation of small quantities of CSF and are unsuitable for the large-scale production. Moreover, in preparing CSF by the conventional methods serum is an indispensable constituent of the medium for cultivating the cells (if the serum is absent in the medium, no CSF will be produced) and bovine serum or fetal calf serum has conventionally been used. In order to avoid the side effects caused by the foreign proteins contained in these media, it is necessary to remove said proteins after cultivation of the cells or to use human serum. The removal of such proteins from the CSF produced in the medium requires a troublesome procedure and is difficult, while the human serum has a disadvantage of expensiveness which results in increased production cost.

As described above, despite the fact that the uses of CSF as a pharmaceutical and as a diagnostic reagent were known, no method has heretofore been developed for the large-scale, low-cost production of a CSF product having no side effects.

An object of this invention is to provide a method which permits a large-scale production of CSF having no side effects and useful as a curative for the human granulocytopenia and as a diagnostic reagent for the myelogenous leukemia.

According to this invention, there is provided a method for producing a substance capable of stimulating the proliferation and differentiation of human granulopoietic stem cells, which comprises cultivating monocytes and macrophages, which have been isolated from the human peripheral blood, in a synthetic medium for tissue culture containing a glycoprotein isolated from human urine and capable of stimulating human or mouse bone marrow cells to form human granulocytes or mouse macrophages and granulocytes, thereby producing an active substance in the medium, and recovering the active substance from the medium.

The glycoprotein capable of stimulating the formation of human granulocytes [hereinafter referred to as glycoprotein (H)] which is isolated from human urine and used in this invention, is fully described in Japanese patent application Laid-open No. 140,707/79, West German Patent "Offenlegungsschrift No. 2,910,745" and U.K. patent application Publication No. 2,016,477. A glycoprotein capable of stimulating the formation of mouse macrophages and granulocytes [herein referred to as glycoprotein (M)], which was isolated from human urine, was described as a known sialic acid-containing glycoprotein by Stanley and Metcalf, Australian Journal of Experimental Biological Medical Science, 47, 467–483 (1969); Stanley et al., Federation Proceedings, 34, No. 13, 2272–2278 (1975); Laukel et al., Journal of Cellular Physiology, 94, 21–30 (1978) and others.

The synthetic medium for tissue culture used in this invention can be a commercial synthetic medium for use in tissue culture or cell culture such as, for example, McCoy's 5A medium [McCoy, T. A., Maxwell, M., and Kruse, P. F.: Proc. Soc. Exper. Biol. and Med., 100: 115–118 (1959), sold by Gibco Co.], Nutrient Mixture HAMF-10 [Ham, R. G., Exp. Cell Res., 29: 515–526 (1963), sold by Gibco Co.], RPM1-1640 [Iwakata, S., Grace J. T. Jr., N.Y.J. of Med., 64/18: 2279–2282 (Sept. 15, 1964), sold by Nissui Seiyaku Co.], or amino acid-supplemented Eagle's MEM medium [Eagle, H., Science 130: 432 (1959), sold by Nissui Seiyaku Co.].

The method of this invention is described below in detail.

(1) Isolation of monocytes and macrophages.

Blood collected from the vein of healthy individuals by means of a heparinized syringe is placed in a sterile test tube and left standing at room temperature for 1 to 2 hours. Subsequent procedures are all conducted under aseptic conditions. After standing, the upper leukocyte layer is collected, washed once with a synthetic medium for tissue culture, and subjected to the density gradient centrifugal precipitation [Mahmood, T. and W. A. Robinson, Blood, 51, No. 5,879–887 (1978)] to fractionate into a layer containing monocytes, macrophages and lymphocytes and another layer containing granulocytes. The former layer is collected to obtain a cell fraction. The cell fraction is suspended in a commercial synthetic medium for tissue culture (hereinafter referred to simply as medium) and centrifuged to remove and reject the supernatant. The cells thus collected are washed by adding the same medium as used above. The washing is repeated at least twice. The washed cells are suspended in a small volume of the same medium. A portion of the resulting suspension is withdrawn and the number of cells is measured with an automatic blood cell counter. The ratio in number of monocytes and macrophages to lymphocytes is determined by the microscopic examination of a smear specimen treated with a Wright-Giemsa's stain. The cell suspension is spread over a Petri dish made of glass or a plastic so that the number of inocula (monocytes and macrophages) may amount to the prescribed value, preferably $10^5$ to $10^7$ per dish, then added with a commercial synthetic medium for tissue culture supplemented with 5 to 20% (volume % based on the medium; the same applies hereinafter) of serum, and allowed to stand at 37° C. in a humidified atmosphere of 5% $CO_2$ in air for 1 to 2 hours. During the period of standing, monocytes and macrophages are adhered onto the bottom surface of the dish, while lymphocytes remain suspended in the medium. The medium is then discarded and the dish is washed several times by adding a medium containing no serum or a physiological saline. After the treatment, most of the lymphocytes are removed, whereas monocytes and macrophages remain adhered onto the bottom surface of the dish. On microscopic examination, it will be found that 95% or more of the cells adhered onto the bottom surface are monocytes and macrophages and the number amounts to $10^5$–$10^7$ per dish.

(2) Cultivation of monocytes and macrophages.

To the above culture dish, is added a synthetic medium with or without supplemented serum and containing at least 0.1 μg/ml (medium) of glycoprotein (H) or glycoprotein (H)-containing fraction, or at least 500 units/ml (medium) of glycoprotein (M) or a glycoprotein (M)-containing fraction (the glycoprotein unit is described later) so that the population density of monocytes and macrophages may become at least $10^5$/ml (medium). The inoculated medium is incubated at 37° C. in a humidified atmosphere of 5% $CO_2$ in air for 1 to 7 days to produce CSF in the medium. The synthetic medium used above is the aforementioned commercial medium for tissue culture.

The optimal conditions for the production of CSF according to this invention with respect to the duration of cultivation, amount of the glycoprotein to be added, amount of cells to be inoculated, amount of serum to be incorporated, and the type of medium are described later in the Experimental Examples.

In preparing CSF for the pharmaceutical use according to this invention, a medium with supplemented human serum or a serum-free medium is used in order to avoid side effects caused by foreign proteins. In preparing CSF for use as a diagnostic reagent, on the other hand, a medium added with bovine serum or fetal calf serum may be used. It is also possible to use a culture bottle in place of the culture dish. Further, those monocytes and macrophages which have undergone cultivation may repeatedly used.

(3) Glycoprotein to be added to a medium.

The glycoprotein used in the method of this invention is that isolated from human urine and capable of stimulating the formation of human granulocytes or mouse macrophages and granulocytes or a fraction containing such glycoprotein.

The glycoprotein capable of stimulating the formation of human granulocytes may be obtained according to the description in the Japanese patent application Laid-open No. 140,707/79 and the other patent publications, as outlined below.

Fresh urine collected from healthy individuals is adjusted to pH 6–9, preferably 7–8, with dilute acid or alkaline solutions and centrifuged to remove the impurities contained in the urine. The supernatant thus obtained is contacted with a silicon-containing adsorbent such as, for example, silica gel, silica gel-magnesium silicate, diatomaceous earth, silica glass or bentonite and the adsorbed components are eluted with an alkaline solution of preferably pH 9 or higher. The alkaline solution used for the elution is not specific but is preferably an aqueous solution of ammonium hydroxide, sodium hydroxide or the like in a concentration of 0.3 to 1.5 M. The eluate thus obtained is adjusted to pH 7–8 and added with a neutral salt such as, for example, ammonium sulfate to 70% saturation to salt out the active substance, whereby a crude fraction containing glycoprotein is obtained.

The above crude fraction is redissolved in a small portion of an alkaline solution, freed from low molecular substances having a molecular weight of 10,000 or less by ultrafiltration and contacted with a cation exchanger (for example, carboxymethyldextran, carboxymethylcellulose or phosphocellulose) to remove the impurities contained in the solution. Before the above contact, both the crude fraction containing glycoprotein and the ion exchanger are equilibrated to pH 6–8 with preferably 0.01–0.15 M buffer solution so that the contact may be carried out under the conditions of nearly neutral pH. Most of the glycoprotein passes through the ion exchanger unadsorbed. After concentration, the concentrated effluent is equilibrated with a dilute buffer solution of pH 6–8 and applied to anion exchanger column (for example, DEAE-cellulose) equilibrated with same buffer as above to adsorb the glycoprotein on the column. The adsorbed glycoprotein is eluted by the so-called linear concentration gradient elution by using a 0.1 to 0.3 M saline solution, e.g. a sodium chloride solution. The glycoprotein is eluted at a salt concentration of 0.1 M or higher, but a perfect separation is difficult. The effluent fractions at 0.1–0.3 M salt concentrations are pooled and, if necessary, the pooled fraction is desalted and concentrated (this fraction is designated fraction A). The fraction A may be used as such in the method of this invention.

It is also possible that before being subjected to the linear concentration gradient elution, the glycoprotein fraction is purified by the adsorption on an anion exchanger and step-wise elution with 0.1–0.3 M saline solution.

For the purpose of further purification, the fraction A obtained above is subjected to gel filtration chromatography on a highly crosslinked polymer gel having a water regain value of 10–20 ml/g such as, for example, Sephadex ® G-150 or Biogel ® P-100; the active substances are developed with a 0.05–0.1 M saline buffer and fractions having a relative effluent value of 1.11–1.60, preferably 1.11 ∝ 1.45, are collected, desalted and concentrated or lyophilized (this fraction is designated fraction B).

The glycoprotein-containing fraction B thus obtained can also be used in the method of this invention. The relative effluent volume as herein referred to is a volume expressed by the ratio $V_e/V_o$ (where $V_e$ represents the volume of solvent necessary to elute the substance in the column and $V_o$ represents the void volume of the gel column).

For further purification, the semi-purified substance obtained above is dissolved in a dilute buffer solution containing 1.0–2.0 M salt such as, for example, a phosphate buffer solution at pH 6.0–8.0, preferably 6.0–7.0, containing 1.0–2.0 M sodium chloride and subjected to affinity chromatography with a sugar affinitive adsorbent such as, for example, concanavalin A—Sepharose 4B (supplied by Pharmacia Fine Chemicals) which has been equilibrated with the same buffer solution. The glycoprotein adsorbed on the affinity column is eluted with a 1.0–2.0 M saline in dilute buffer at pH 6.0–8.0, preferably 6.0–7.0, containing 20–100 mM saccharide (for example, α-methyl-D-glucoside). The fractions containing glycoprotein are combined and, if necessary, desalted and concentrated or lyophilized. This fraction can also be used in the present method.

For still further purification, the above fraction is subjected to preparative zone electrophoresis using as the supporting medium, for example a polyacrylamide gel or agar gel, pH 7.0–9.0, and a highly purified glycoprotein fraction is recovered from the supporting medium with a dilute saline solution under cooling. This fraction is desalted and concentrated or lyophilized. The purified glycoprotein can also be used in the method of this invention.

The glycoprotein used in the present method, which stimulates the formation of mouse granulocytes and macrophages has been described in the afore-mentioned literature. The preparative method of Stanley and Metcalf, that of Stanley et al. and that of Laukel et al. are described in detail in Examples 6, 5 and 7, respectively, in this specification.

The biological activity of the glycoprotein preparations to mouse bone marrow cells is assayed in the following way and expressed in terms of "unit." To 1 ml of McCoy's 5A medium supplemented with 20% of fetal calf serum, 0.3% of agar and $1 \times 10^5$ bone marrow cells of $C_{57}Bl/6J$ mice, is added with 0.1 ml of glycoprotein being assayed or a fraction containing same. The glycoprotein-containing medium thus prepared is placed in a plastic Petri dish, 35 mm in diameter, and incubated at 37° C. in a humidified atmosphere of 5% $CO_2$ in air for 7 days. After completion of the incubation, the number of discrete colonies containing each 50 or more cells is counted with an inverted microscope. The biological activity of a sample forming one colony is assumed to be one unit. To evaluate the purification degree of a glycoprotein sample, the specific activity is calculated by the following equation:

$$\text{Specific activity} = \frac{\text{Unit of the sample}}{\text{Quantity of glycoprotein or fraction containing glycoprotein (mg)}}$$

The specific activity increases with the progress of purification. The glycoprotein or glycoprotein-containing fraction being added to the medium in the method of this invention can be purified one having a high specific activity but is preferably one having a rather lower activity obtained in the course of purification. The quantities of glycoprotein(H) and (M) to be added to the medium are at least 0.1 μg, preferably 10–100 μg per 1 ml of medium, and at least 500 units, preferably 1000 units or more per 1 ml of medium, respectively.

(4) Recovery of the active substance from the conditioned medium.

The conditioned medium containing CSF prepared as described above is collected from the Petri dish and centrifuged at 1,000–2,000×g for 5 to 10 minutes to obtain a supernatant which contains highly active CSF.

The above supernatant is useful for the preparation of a clinical diagnostic reagent or a reference reagent for testing the formation of colonies by human granulopoietic stem cells. For this purpose, the activity of the supernatant is adjusted so that 0.1 ml of the supernatant may contain a CSF activity sufficient for forming at least 100 human granulocyte colonies, filtered through a membrane filter, aseptically filled in a container and hermetically sealed to obtain a liquid reagent. A reagent in powder form can be prepared by the aseptic lyophilization of the above sterile filtrate.

For the pharmaceutical use, a conditioned medium obtained by using a serum-free medium or a human serum supplemented medium is dialyzed against water to remove medium constituents, and sterilized by membrane filtration. If necessary, the filtrate is concentrated, aseptically filled in a container and hermetically sealed to obtain a pharmaceutical in liquid form. It is also possible to obtain a pharmaceutical in powder form by sterilizing the dialyzed solution by membrane filtration and lyophilizing aseptically.

For further purification of CSF for the pharmaceutical use, the aforementioned supernatant is separated into a high molecular fraction (molecular weight above 5,000 or 10,000) and a low molecular fraction (molecular weight below 5,000 or 10,000) by means of an ultrafiltration membrane (molar weight cutoff 5,000 or 10,000). Although both fractions contain CSF, 90% or more of CSF exist in the high molecular fraction.

A pharmaceutical product can be obtained by concentrating the low molecular fraction in vacuo. The concentrate of high molecular fraction is dissolved in 0.01–0.1 M buffer solution (pH 6.0–8.0) and contacted with an anion exchange resin such as, for example, DEAE-cellulose, DEAE-Sephadex or QAE-Sephadex, which has been equilibrated with the said buffer solution, to adsorb CSF on the resin. The CSF adsorbed on the resin is eluted with 0.1–0.3 M buffer solution (pH 6.0–8.0) to obtain a purified product.

The above eluate can be further purified by concentration and subsequent molecular sieve chromatography by gel filtration. The gel for the gel filtration can be any of commerical Sephadex ® G-150, Biogel ® P-100 and Ultrogel ® ACA-44.

When the CSF activity is produced by using a serum-free medium, the treatment with an anion exchange resin can be omitted and the purification is performed directly by the gel filtration chromatography. A suitable developing buffer solution in the gel filtration chromatography is 0.01–0.3 M buffer solution (pH 6.0–8.0). The CSF activity fractions obtained by gel filtration are pooled and the pooled fraction is concentrated, desalted and lyophilized to yield a purified CSF product.

The purified CSF products obtained above are analyzed for the contaminant proteins by immunoelectrophoresis using human antiserum and bovine antiserum. Trace amounts of human globulin-like proteins and serum albumin and globulin-like proteins both originated presumably from fetal calf serum are detected in the CSF products obtained from a fetal calf serum supplemented medium. On the other hand, since absolutely none of such proteinic substances is detectable in the CSF produced in the serum-free medium, it may be used as a pharmaceutical which is free from side effects.

For injections, the liquid pharmaceutical products are used as such and the powder products are suitably dissolved in sterile water, sterile physiological saline, or the like before use.

The pharmaceutical product prepared by the present method is administered to a patient with granulocytopenia at an effective dose larger than 77.8 mg/kg body weight/day.

EXPERIMENTAL EXAMPLE 1

Experiment on incubation period.

(1) Isolation of monocytes and macrophages and preparation of glycoprotein.

Monocytes and macrophages were isolated as described later in Example 1-(1). The glycoproteins used in the experiment were prepared as described later in Example 1-(2) and Example 5-(2). The glycoprotein (H) prepared as in Example 1-(2) was a highly purified product in the final purification stage and the glycoprotein (M) prepared as in Example 5-(2) was a standard purity product (specific activity: 180,000).

(2) Incubation of monocytes and macrophages.

Two media each containing 100 µg/ml of glycoprotein (H) and two glycoprotein-free media were prepared. For the media, were used serum-free McCoy's 5A medium and supplemented McCoy's 5A medium containing 20% of fetal calf serum.

To each Petri dish containing monocytes and macrophages adhered onto the bottom, was added each one of the four media at a rate of $10^6$ monocytes and macrophages per ml medium. Each medium was incubated in the same manner as in Example 1-(3). A predetermined volume of the medium was withdrawn from each dish before incubation and after incubation periods of 1, 3, 5 and 7 days.

On the other hand, the above procedure was repeated, except that the glycoprotein (M) was used at a rate of 1,000 units/ml medium in place of the said amount of the glycoprotein (H).

(3) Assay of CSF in the conditioned medium.

The CSF activity of each conditioned medium was assayed by the formation of colonies of human bone marrow cells. The bone marrow was withdrawn from the sternum of a healthy individual by means of a heparinized syringe after sternal puncture. The withdrawn bone marrow was centrifuged at 1,000×g for 10 minutes to collect the buffy coat. The buffy coat was washed with McCoy's 5A medium, suspended in McCoy's 5A medium containing 20% of serum, spread over a Petri dish, added with several mg/ml medium of a powdered carbonyl-iron which had been subjected to dry air sterilization, and allowed to stand in an incubator at 37° C. for 1 to 2 hours. After standing, the phagocytic cells which phagocytized the particles of carbonyl-iron were fixed to the bottom of Petri dish by means of a magnet and the supernatant cell suspension was collected. The suspended cells are now adherent, non-phagocytic bone marrow cells and are used for the assay of CSF activity. These bone marrow cells were washed by centrifugation and suspended in a small volume of the medium. The number of nucleated cells in the suspension was counted after treating with an acetic acid-gentain stain.

The non adherent, non-phagocytic nucleated cells were added to McCoy's 5A medium containing 0.3% of agar and 20% of fetal calf serum so that the medium may contain $2 \times 10^5$ said cells per ml of the medium. After addition of the conditioned medium at a rate of 0.1 ml/ml medium, the inoculated medium was incubated at 37° C. in a humidified atmosphere of 5% $CO_2$ in air for 10 days. After incubation the number of colonies among the cell aggregates which were formed was counted under a microscope (the term "colony", as herein used, means a cell aggregate containing 40 or more cells). The CSF activity was expressed in terms of the number of colonies and used as a measure for the production of CSF. The results were as shown in Table 1.

TABLE 1

| Cultivation conditions | CSF activity (number of colonies) per 0.1 ml of conditioned medium | | | |
|---|---|---|---|---|
| | Medium containing 20% of fetal calf serum | | Serum-free medium | |
| Period of incubation (day) | Glycoprotein added | Glycoprotein not added | Glycoprotein added | Glycoprotein not added |
| Glycoprotein (H) | | | | |
| Before incubation | 0 | 0 | 0 | 0 |
| 1 | 13 ± 3 | 3 ± 1 | 2 ± 1 | 0 |
| 3 | 116 ± 4 | 24 ± 3 | 25 ± 2 | 1 ± 1 |
| 5 | 117 ± 3 | 23 ± 1 | 20 ± 1 | 0 |
| 7 | 98 ± 1 | 16 ± 4 | 18 ± 1 | 0 |
| Glycoprotein (M) | | | | |
| Before incubation | 0 | 0 | 0 | 0 |
| 1 | 20 ± 8 | 6 ± 4 | 0 | 0 |
| 3 | 89 ± 6 | 29 ± 8 | 35 ± 4 | 3 ± 1 |
| 5 | 86 ± 3 | 30 ± 4 | 30 ± 6 | 4 ± 1 |
| 7 | 69 ± 4 | 16 ± 2 | 23 ± 4 | 2 ± 1 |

As shown in Table 1, it was found that by the addition of either glycoprotein the CSF production became nearly maximum on the third day of incubation in every medium. In the medium containing 20% of fetal calf serum, the CSF production was markedly larger in the presence of glycoprotein than in the absence of glycoprotein (conventional method). In the serum-free medium CSF was produced when glycoprotein was added, while CSF was scarcely produced when glycoprotein was not added.

From the above results, it is evident that in producing CSF by the cultivation of monocytes and macrophages in vitro, these glycoproteins stimulate the production of CSF, whether the medium contains serum or not. It was also found that a suitable incubation period is 3 to 7 days, preferably 3 days. It is to be noted that when monocytes and macrophages were not needed, no CSF activity was detected in the conditioned medium, whether glycoprotein was present or not.

EXPERIMENTAL EXAMPLE 2

Experiment on the amount of glycoprotein added to the medium.

Media were prepared by adding the same glycoproteins (H) and (M) as used in Experimental Example 1 to McCoy's 5A medium supplemented with 20% of fetal calf serum and serum-free McCoy's 5A medium. In the case of glycoprotein (H), the amount added to the medium was 0.1, 1.0, 10.0 or 100 μg/ml medium. In the case of glycoprotein (M), the added amount was 100, 500, 1,000 or 2,000 units/ml medium. Each prepared medium was poured into the Petri dish containing adhered monocytes and macrophages and incubated for 3 days in the same manner as in Experimental Example 1. The CSF activity of each conditioned medium was assayed as in Experimental Example 1 to examine the CSF production. Samples obtained by incubating each medium without the addition of glycoprotein were used as control. The results obtained were as shown in Table 2.

TABLE 2

| Added amount of glycoprotein | CSF activity (number of colonies) per 0.1 ml of conditioned medium | |
|---|---|---|
| | Medium containing 20% of fetal calf serum | Serum-free medium |
| Glycoprotein (H) (μg/ml) | | |
| 0 (control) | 24 ± 3 | 1 ± 1 |
| 0.1 | 51 ± 2 | 9 ± 1 |
| 1.0 | 116 ± 4 | 25 ± 2 |
| 10.0 | 166 ± 10 | 53 ± 3 |
| 100.0 | 170 ± 8 | 80 ± 4 |
| Glycoprotein (M) (unit/ml) | | |
| 0 (control) | 21 ± 6 | 2 ± 1 |
| 100 | 28 ± 3 | 6 ± 3 |
| 500 | 96 ± 10 | 13 ± 6 |
| 1000 | 129 ± 8 | 49 ± 6 |
| 2000 | 170 ± 6 | 85 ± 8 |

As is seen from Table 2, by the addition of either glycoprotein the CSF production increased with the increase in the added amount of glycoprotein. In view of the above results as well as the previous results shown in Table 1 (results obtained by 3 days incubation), it is acceptable that CSF production is markedly increased by the presence of 0.1 μg of glycoprotein (H) or 500 units of glycoprotein (M) in 1 ml of the medium. In the present method, therefore, the amount of glycoprotein to be added to 1 ml of the medium is at least 0.1 μg, preferably 10 to 100 μg for glycoprotein (H) and at least 500 units, preferably 1,000 units or more for glycoprotein (M).

EXPERIMENTAL EXAMPLE 3

Experiment on the amount of monocytes and macrophages to be inoculated into the medium.

A series of conditioned media were obtained by repeating the procedure of Experimental Example 1, except that the number of monocytes and macrophages inoculated into 1 ml of the medium was 0, $10^3$, $10^4$, $10^5$ or $10^6$; 1 μg of the glycoprotein (H) or 500 units of the glycoprotein (M) was added to 1 ml of McCoy's 5A medium supplemented with 20% of fetal calf serum or serum-free McCoy's 5A medium; and the incubation period was 3 days. The conditioned media obtained were assayed for the CSF activity to examine the production of CSF in the same manner as in Experimental Example 1. The experimental results were as shown in Table 3.

TABLE 3

| Number of cells inocubated (number/ml) | CSF activity (number of colonies) per 0.1 ml of conditioned medium | |
|---|---|---|
| | Medium containing 20% of fetal calf serum | Serum-free medium |
| Medium containing glycoprotein (H) | | |
| 0 | 0 | 0 |
| $10^3$ | 13 ± 1 | 0 |
| $10^4$ | 20 ± 2 | 6 ± 1 |
| $10^5$ | 116 ± 4 | 25 ± 2 |
| $10^6$ | 185 ± 7 | 69 ± 5 |
| Medium containing glycoprotein (M) | | |
| 0 | 0 | 0 |
| $10^3$ | 19 ± 6 | 0 |
| $10^4$ | 29 ± 10 | 8 ± 4 |
| $10^5$ | 98 ± 6 | 31 ± 3 |
| $10^6$ | 169 ± 9 | 74 ± 2 |

As is evident from Table 3, in any of the media used in the experiment, a large quantity of CSF were produced when at least $10^5$ cells were present in 1 ml of the medium. In the method of this invention, therefor, it is desirable to inoculate at least $10^5$ monocytes and macrophages into 1 ml of the medium.

EXPERIMENTAL EXAMPLE 4

Comparative experiments of CSF production on several media.

With respect to the CSF production, four commercially available media for tissue culture or cell culture were compared with one another. The media used in the experiment included McCoy's 5A medium (Gibco Co.), nutrient mixture HAMF-10 (Gibco Co.), RPMI-1640 (Nissui Seiyaku Co.), and Eagle's MEM medium supplemented with amino acids (Nissui Seiyaku Co.).

To each of the media containing no supplemented serum, was added 1.0 μg/ml medium of the glycoprotein (H) or 500 units/ml medium of the glycoprotein (M). The prepared media were incubated for 3 days in the same manner as in Experimental Example 1. The conditioned media were assayed for CSF activity in the same manner as in Experimental Example 1 to examine the CSF production. The results obtained were as shown in Table 4.

TABLE 4

| Medium | CSF activity (number of colonies) per 0.1 ml of conditioned medium | |
|---|---|---|
| | Added with glycoprotein (H) | Added with glycoprotein (M) |
| McCoy's 5A | 69 ± 5 | 83 ± 6 |
| HAMF - 10 | 71 ± 3 | 76 ± 8 |
| RPMI - 1640 | 75 ± 3 | 81 ± 1 |
| MEM | 48 ± 1 | 46 ± 5 |

As is evident from Table 4, any of the above four media can be used in carrying out the method of this invention, though the CSF production is somewhat lower in the MEM medium.

EXPERIMENTAL EXAMPLE 5

Experiment on the amount of serum added to the medium.

Conditioned media were obtained in the same manner as in Experimental Example 1, except that use was made of those media which had been prepared by adding to McCoy's 5A medium, 0, 5, 10, 20 or 30% of human serum (Green Cross Co.) or fetal calf serum (Flow Laboratory Co.), both of which had been heated at 58° C. for 30 minutes, followed by 1 μg/ml medium of the glycoprotein (H) or 500 units/ml medium of the glycoprotein (M); the number of monocytes and macrophages inoculated into each medium was $10^5$/ml; and the period of incubation was 3 days. The conditioned media obtained were assayed for CSF activity in the same manner as in Experimental Example 1 to examine the production of CSF. The results were as shown in Table 5.

TABLE 5

| Added amount of serum (%) | CSF activity (number of colonies) per 0.1 ml of conditioned medium | |
|---|---|---|
| | Added with human serum | Added with fetal calf serum |
| Medium containing glycoprotein (H) | | |
| None | 25 ± 2 | 25 ± 2 |
| 5 | 55 ± 1 | 43 ± 1 |
| 10 | 120 ± 5 | 98 ± 3 |
| 20 | 150 ± 3 | 116 ± 4 |
| 30 | 141 ± 2 | 108 ± 2 |
| Medium containing glycoprotein (M) | | |
| None | 21 ± 8 | 21 ± 8 |
| 5 | 49 ± 6 | 51 ± 4 |
| 10 | 109 ± 5 | 89 ± 2 |
| 20 | 124 ± 7 | 102 ± 6 |
| 30 | 123 ± 8 | 92 ± 5 |

As is apparent from Table 5, with the increase in the amount of either serum added to the medium, the production of CSF was found to increase. Although according to this invention CSF is produced in a serum-free medium, bovine serum or fetal calf serum can be added to the medium when the production of a large amount of CSF is required for use as a reagent. The effective amount of serum to be added for such a purpose is at least 5%, preferably 10% or more.

EXPERIMENTAL EXAMPLE 6

Experiment on the addition of a glycoprotein-containing fraction and a highly purified fraction.

In Experimental Examples 1 to 5, purified glycoprotein was used as the active substance having a stimulating effect on the formation of human granulocytes (Case I) and, on the other hand, standard purity glycoprotein (specific activity: 180,000) was used as the active substance having a stimulating effect on the formation of mouse macrophages and granulocytes (Case II). The present experiment was carried out, as described below, to demonstrate that in the method of this invention a semi-purified material can be used in place of the purified glycoprotein in Case I and that a less purified fraction as well as a highly purified material can be used in place of the standard purity glycoprotein in Case II.

The glycoprotein-containing fractions used in the experiment corresponding to Case I were the fractions A and B prepared as described later in Example 1. These fractions were each added to serum-free McCoy's 5A medium in varied amounts of 0, 0.5, 1.0, 5.0 and 10 mg/ml corresponding, respectively, to 0, 8.3, 16.6, 83.3 and 166.6 μg/ml medium in terms of active glycoprotein in fraction A and 0, 41.7, 83.4, 417 and 834 μg/ml medium in terms of active glycoprotein in fraction B. The number of monocytes and macrophages inoculated into each medium was $10^5$/ml and the incubation period was 3 days. Conditioned media were obtained by incubating under otherwise the same conditions as in Experimental Example 1.

Since the fractions A and B contained human serum albumin excreted into the urine, control samples were prepared by adding human serum albumin (Sigma Co.) to McCoy's 5A medium in an amount corresponding to that contained in the media prepared above; incubation conditions were the same as described above.

Each conditioned medium was assayed for the CSF activity in the same manner as in Experimental Example 1 to examine the production of CSF. The results obtained were as shown in Table 6.

As for the Case II, the glycoprotein materials used in the present experiment were the fraction C (specific activity: 21,000), fraction D (specific activity: 54,000) and the highly purified material (specific activity: 1,240,000) described in Example 5 and prepared as in Example 5. Conditioned media were obtained by repeating the experimental procedure described above in connection with Case I, except that the fractions C and D and the highly purified material (see Example 5) were each added to the media in varied amounts of 0, 100, 500, 1,000 and 2,000 units/ml medium in place of the described amounts of the fractions A and B (see Example 1) and the control tests using human serum albumin were omitted. The results obtained were as shown in Table 6.

TABLE 6

| Added amount | CSF activity (number of colonies) per 0.1 ml of conditioned medium | | |
|---|---|---|---|
| Glycoprotein of Example 1 (mg/ml) | Fraction A | Fraction B | Control |
| None | 0 | 0 | 0 |
| 0.5 | 60 ± 1 | 59 ± 1 | 4 ± 1 |
| 1.0 | 121 ± 1 | 114 ± 1 | 6 ± 2 |
| 5.0 | 170 ± 3 | 103 ± 3 | 14 ± 2 |
| 10.0 | 148 ± 2 | 98 ± 4 | 26 ± 1 |
| Glycoprotein of Example 5 (units/ml) | Fraction C | Fraction D | Highly purified material |
| None | 2 ± 1 | 2 ± 1 | 2 ± 1 |
| 100 | 8 ± 2 | 10 ± 4 | 5 ± 2 |
| 500 | 36 ± 6 | 37 ± 4 | 10 ± 3 |
| 1000 | 74 ± 5 | 66 ± 5 | 21 ± 4 |
| 2000 | 122 ± 8 | 113 ± 6 | 44 ± 9 |

Effect of the purification degree of the glycoprotein having a stimulating effect on the formation of human granulocytes: The CSF production in a medium added with fraction A or B was higher than that in the control medium, indicating that glycoprotein stimulates the CSF production. As compared with the example shown in Table 2, wherein 10 μg/ml of glycoprotein was added to the serum-free medium, CSF production was higher in the example shown in Table 6, wherein 0.5 mg/ml of the fraction A (8.3 μg/ml in terms of glycoprotein) was added, though a small amount of glycoprotein was added in the latter example. This seems to be due to the influence of serum albumin and other unknown ingredients of the human urine contained in the fraction A.

By comparison of the medium added with fraction A with that added with fraction B with respect to CSF production, it is seen that when the added amount is at a level of 0.5 or 1.0 mg/ml, both fractions are comparable to each other, but at higher levels the fraction B shows lower CSF production. This is probably because the human urinary serum albumin content of A is larger than that of B and because the addition of fraction B in an amount larger than 5 mg/ml results in excessive addition of glycoprotein. By taking these results collectively into account, it is presumable that the serum alubumin and the like contained in human urine and the glycoprotein act synergetically in promoting the CSF production and that a maximum CSF production is attained when about 100 μg/ml of glycoprotein is added to the medium.

As for the glycoprotein having a stimulating effect on the formation of mouse macrophages and granulocytes (Case II), it is apparent from Table 6 that in every case the CSF production increased approximately in proportion to the amount of glycoprotein added to the medium. As compared with the results shown in Table 2 obtained by using a serum-free medium, the CSF production was higher in the case of the present experiment, wherein fraction C or D was used, although the amount of glycoprotein added to the medium is the same as in the former case. This seems to be caused by the influence of the serum albumin and the like contained in the fractions C and D which are originated from human urine. From the results obtained by adding a highly purified glycoprotein material, it is apparent that although the CSF production is increased with the increase of said glycoprotein material, the increment is less than that in the cases of fractions C and B and the standard purity material (Table 2). From the above results, it is presumable that in serum-free media, serum albumin and other substances originated from human urine play the same role as that of serum with respect to CSF production.

In every case, therefore, in order to operate advantageously the method of this invention, it is preferable to add to the medium a crude glycoprotein rather than to add a purified glycoprotein. In adding a crude glycoprotein material, it is added in an amount of at least 0.1 μg/ml medium in Case I or at least 500 units/ml medium in Case II.

EXPERIMENTAL EXAMPLE 7

Experiment on effective dose, etc.

The effective dose and the acute toxic dose (LD$_{50}$) of CSF produced by the method of this invention were determined by the following animal test.

A conditioned medium prepared in the same manner as in Example 3 was sterilized by membrane filtration, then filtered through an ultrafiltration membrane (molecular weight cut off: 10,000), concentrated, desalted, and lyophilized to obtain CSF in powder form. Upon testing by the same method as used in Experimental Example 1, the number of colony formation with human bone marrow cells was found to be 4,500/mg. For comparison, the test was repeated using C3H/He mouse bone marrow cells and the number of colony formation with the mouse bone marrow cells was found to be 7,000/mg.

Eighty C3H/He male mice (6 weeks old and 20 g of average body weight) were divided at random into 16 subgroups of each 5 members. The subgroups were assembled at random to form 4 groups of each 4 subgroups.

The CSF obtained above was dissolved in sterile physiological saline solution to obtain 3 solutions of 1 mg/0.1 ml (for group II), 2 mg/0.1 ml (for group III), and 4 mg/0.1 ml (for group IV). Each mouse was administered subcutenously with the solution in a dose of 0.1 ml/mouse/day, for 5 consecutive days. After 1, 3, 7 and 11 days from the beginning of administration, blood samples were collected from five mice of one subgroup of each group (the subgroups from which the blood samples had been collected were exempted from the further test). The number of leukocytes in the peripheral blood were counted by the automatic blood cell counter and the number of granulocytes were counted under microscope by Wright-Gimsa's stained smears to determine the increase in the number of leukocytes and granulocytes resulted from the administration of CSF. A group (group I) administered with 0.1 ml of a sterile physiological saline containing no CSF was treated in the same manner as above and used as the control group. The experimental results were as shown in Table 7.

TABLE 7

| Group No. Period of test (day) | I (control) | | II | | III | | IV | |
|---|---|---|---|---|---|---|---|---|
| | Leukocyte | Granulocyte | Leukocyte | Granulocyte | Leukocyte | Granulocyte | Leukocyte | Granulocyte |
| 1 | 55 ± 20 | 14 ± 7 | 53 ± 4 | 13 ± 8 | 51 ± 5 | 16 ± 4 | 59 ± 8 | 20 ± 5 |
| 3 | 59 ± 7 | 12 ± 8 | 63 ± 9 | 18 ± 4 | 98 ± 10 | 40 ± 10 | 123 ± 6 | 60 ± 8 |
| 7 | 41 ± 8 | 12 ± 4 | 74 ± 8 | 28 ± 6 | 140 ± 8 | 60 ± 9 | 201 ± 5 | 102 ± 14 |
| 11 | 58 ± 8 | 15 ± 6 | 102 ± 9 | 45 ± 10 | 185 ± 14 | 75 ± 13 | 260 ± 19 | 121 ± 21 |

Note:
1. The numericals here present the values of (blood cell number per 1 mm$^3$ of blood × 10$^{-2}$).
2. Each experimental result, shown, is the average on 5 mice.

As compared with group I (control), among the CSF administered groups group II showed a twice increase in the number of leukocytes and a nearly three times increase in the number of granulocytes after 11 days from the beginning of test (6 days after the termination of administration). As compared with group I, group IV showed a remarkable increase of about 4.5 times in the number of leukocytes and about 8 times in the number of granulocytes. From the above results an effective dose in mice may be assumed to be 50 mg/kg body weight/day. Since the colony-forming activity of the CSF employed in the above experiment is higher in the mouse bone marrow cells than that in human bone marrow cells by a factor of 1.556, an effective dose for a patient with granulocytopenia which exhibits on human bone marrow cells an effect equivalent to the effect in mice is about 77.8 mg/kg body weight/day.

The acute toxicity of CSF prepared according to this invention was tested by employing the same CSF as used in the above test for administration dose and C3H/He mice (6–8 weeks old and an average body weight of 20.4 g). No fatal case was found in a group (5 male and 5 female members) administered with 4.0 g of CSF/kg body weight. Accordingly, the acute toxicity was too weak to be determined by the above test.

EXAMPLE 1

(1) Isolation of monocytes and macrophrages.

Two hundred milliliters of periphery blood from normal humans were collected in a blood collecting bottle containing 1,000 units of heparin and allowed to mix together with gently movement. The heparinized blood was transferred to a sterile glass cylinder, 20 mm in diameter and 200 ml in volume, and allowed to stand for 2 hours at room temperature. After standing, the upper leukocyte layer was collected carefully with a pipet, diluted with serum-free McCoy's 5A medium to twice the original volume, centrifuged at 1,500×g for 15 minutes. The supernatant was discarded and the sediment was suspended in 20 ml of McCoy's 5A medium, superposed over a sodium metrizoate solution (specific gravity, d=1.077) in a centrifuge tube, and centrifuged at 400× g for 30 minutes. The white layer containing monocytes, macrophages and lymphocytes at the bottom of the upper layer was collected with a pipet, washed by adding McCoy's 5A medium, centrifuged at 1,500×g for 10 minutes, and the supernatant was discarded. This treatment was repeated twice more. The cells thus obtained were suspended in 20 ml of McCoy's 5A medium and a portion was used for counting the number of cells with an automatic blood cell counter (Toa manufacturing Co.). A smear specimen of the suspension was prepared, stained with Wright-Giemsa's stain, and the number of lymphocytes as well as the number of monocytes and macrophages were morphologically counted to determine the cell ratio. The proportion of monocytes and macrophages was found to be 25.5%.

A 5 ml aliquot of the suspension was placed in each of the four Petri dishes, 15 cm in diameter, added with 30 ml of McCoy's 5A medium supplemented with 10% of fetal calf serum, and allowed to stand at 37° C. for 2 hours in a humidified atmosphere of 5% carbon dioxide in air. After standing the medium was discarded and 30 ml of McCoy's 5A medium was added, and after rather vigorously shaking, the medium was discarded to remove lymphocytes. The proportion of monocytes and macrophages remained was determined by the same testing method as used above and found to be 95% in every dish.

(2) Preparation of glycoprotein.

Glycoprotein was prepared in the following manner according to the method disclosed in the Japanese patent application Laid-open No. 14,707/79 and the others, mentioned above.

Four hundred liters of fresh urine collected from normal humans was adjusted to pH 8 with 10% sodium hydroxide solution and centrifuged at 15,000×g in a continuous centrifugation at 0° C., whereby the insolubles were removed and the supernatant was collected. The supernatant was adjusted to pH 7 with 10% hydrochloric acid and passed through a column (10×80 cm) packed with silica gel. The components adsorbed on the silica gel were eluted with 40 liters of 5% ammonia water. The eluate thus obtained was adjusted to pH 7.5 with 1 N sulfuric acid, added with powdered ammonium sulfate to 70% saturation, allowed to stand at 0° C. for overnight, and the formed precipitate was collected by filtration.

The precipitate was dissolved in 2 liters of 5% ammonia water, placed in a dialysis tube (Visking Co.) and thoroughly dialyzed against 0.05 M phosphate buffer solution (pH 6.5). The dialyzed solution was made up to 10 liters with said buffer solution, and passed through a CM Sephadex C-50 ion exchanged column (40×40 cm) which had been equilibrated with 0.05 M phosphate buffer solution. The contaminants were removed by adsorption on the ion exchange column and the effluent was collected.

Ten liters of the above effluent was concentrated using Diaflow hollow fiber concentrator (Type DC-30, Amicon Co.) and the concentrate was dialyzed against 0.1 M tris-HCl buffer solution (pH 7.0) for overnight at 5° C. The dialyzed solution was made up to 1 liter with the same buffer solution and passed through the DEAE-cellulose column (4.0×40 cm) which had been equilibrated with the same buffer solution. After washing with 0.1 M tris-HCl buffer solution, the adsorbed components were eluted with 0.1 M tris-HCl buffer solution (pH 7.0) containing 0.3 M sodium chloride. The eluate was collected and dialyzed against 0.1 M tris-HCl buffer solution (pH 7.0).

The dialyzed solution was again passed through the DEAE-cellulose column (4.0×40 cm) which had been activated by equilibrating with the same buffer solution and eluted by the linear concentration gradient elution of NaCl (chloride ion concentration gradient, 0.1–0.3 M) to collect the fractions eluted at chloride ion concentrations covering from 0.15 to 0.25 M. The pooled fraction was added with powdered ammonium sulfate to 70% saturation and the formed precipitate was collected, dissolved in a small portion of 0.1 M tris-HCl buffer solution (pH 7.0) and dialyzed against the same buffer to collect the dialyzed solution (fraction A).

Twenty milliliter of the above dialyzed solution was developed on a Sephadex G-150 column (4.0×60 cm) which had been equilibrated with 0.1 M tris-HCl buffer (pH 7.0) and the fractions corresponding to a relative effluent value of 1.11–1.45 were collected. The combined fraction was thoroughly dialyzed against distilled water and the dialyzed solution was lyophilized to obtain about 500 mg of a powder (fraction B).

Two hundred milligrams of the above powder was dissolved in a 0.02 M phosphate buffer solution (pH 7.0) containing 1.0 M sodium chloride and applied to a concanavalin A-Sepharose 4B affinity column (100 ml) which had been equilibrated with the same buffer solution. The column was washed thoroughly with a 0.02 M phosphate buffer (pH 7.0) containing 1.0 M sodium chloride and then eluted with a 0.02 M phosphate buffer (pH 7.0) containing 50 mM α-methyl-D-glucoside and 1.0 M sodium chloride. The eluate was dialyzed against distilled water and the dialyzed solution was lyophilized.

Further, about 50 mg of the lyophilized powder obtained above was dissolved in 1 ml of a 0.125 M tris-glycine buffer (pH 6.8) containing 10% of glycerol and electrophored at 10 mA under cooling by means of a preparative electrophoresis apparatus (Fuji Kabara-II of Fuji Riken Co.) employing 8% acrylamide gel (pH 8.9; 20×25 mm). The fraction with a relative mobility of 0.46 was recovered with a 0.025 M tris-glycin buffer solution (pH 8.3), then dialyzed against distilled water, and the dialyzed solution was lyophilized to obtaine about 10 mg of glycoprotein. By repeating the above procedure, about 30 mg of glycoprotein were obtained.

(3) Cultivation of monocytes and macrophages.

The glycoprotein obtained above was added to 30 ml of a supplemented McCoy's 5A medium containing 20% of fetal calf serum at a rate of 100 μg/ml medium and 30 ml of the prepared medium was poured into each Petri dish which contained adhered macrophages and monocytes as described in (1) of this example. The number of monocytes and macrophages in the medium was $10^6$/ml medium. The prepared medium was incubated of 37° C. for 3 days in a humidified atmosphere of 5% $CO_2$ in air to obtain conditioned medium containing CSF.

(4) Purification of CSF in the conditioned medium.

The collected medium was centrifuged (2,000×g) at 2° C. for 10 minutes to collect about 120 ml of the clear supernatant which was concentrated by ultrafiltration membrane (Amicon Co.; molar weight cut-off 10,000). The concentrate was added with 100 ml of a 0.05 M tris-HCl buffer solution (pH 7.2) and again concentrated to 5 ml.

The solution obtained above was applied to a DEAE-cellulose column (2.0×60 cm) which had been equilibrated with 0.05 M tris-HCl buffer (pH 7.0) and the CSF was eluted with linear gradient concentration of NaCl (0-3 M). The eluted active fraction was pooled and concentrated by means of the above-said ultrafiltration membrane apparatus. The concentrated solution was applied to a Sephadex G-150 column (2.0×90 cm) which had been equilibrated with a 0.05 M tris-HCl buffer solution (pH 7.0) and then developed with the same buffer solution to collect the fractions corresponding to a molecular weight of 65,000-90,000 and the fractions corresponding to a molecular weight of 30,000-60,000. These fractions were combined and concentrated by the ultrafiltration membrane apparatus. The concentrated solution was added with distilled water, desalted and concentrated to obtain about 5 ml of a solution containing purified CSF. This solution was found to have an activity of forming 41,000 colonies of human granulocytes per ml, as assayed in the same manner as in Experimental Example 1.

EXAMPLE 2

In a manner similar to that in Example 1, monocytes and macrophages were isolated from human peripheral blood and treated with the purified glycoprotein. By using a medium prepared by adding the purified glycoprotein to serum-free McCoy's 5A medium at a rate of 100 µg/ml medium, about 5 ml of a solution containing purified CSF was obtained in a manner similar to that in Example 1. This solution showed an activity of forming 16,000 human granulocyte colonies per ml solution, as assayed in the same manner as in Experimental Example 1.

EXAMPLE 3

In a manner similar to that in Example 1, monocytes and macrophages were separated from the human peripheral blood and treated with the glycoprotein-containing fraction (fraction A). By using a medium prepared by adding said fraction to serum-free McCoy's 5A medium at a rate of 5 mg (83.3 mg in terms of glycoprotein)/ml medium, about 120 ml of a conditioned medium was obtained. The conditioned medium was dialyzed against distilled water and the dialyzed solution was concentrated by vacuum evaporation at low temperatures to obtain about 5 ml of a CSF-containing solution. This solution showed an activity of forming 36,700 human granulocyte colonies per ml of the solution, as assayed in the same manner as in Experimental Example 1.

EXAMPLE 4

In a manner similar to that in Example 1, monocytes and macrophages were separated from the human peripheral blood and treated with the glycoprotein-containing fraction (fraction B). By using a medium prepared by adding said fraction to McCoy's 5A medium containing 10% of human serum at a rate of 1 mg (83.3 µg in terms of glycoprotein)/ml medium, about 5 ml of a purified CSF-containing solution was obtained in a manner similar to that in Example 1. This solution showed an activity of forming 43,200 human granulocyte colonies per ml of the solution, as assayed in the same manner as in Experimental Example 1.

EXAMPLE 5

(1) Preparation of glycoprotein.

According to the method of Stanley et al. described previously, glycoprotein and glycoprotein-containing fractions were prepared in the following manner.

Four hundred liters of fresh urine collected from normal humans was dialyzed against water through an ultrafiltration membrane. The dialyzed solution was adjusted to pH 7.4 and passed through a DEAE-cellulose column (20×15 cm) which had been equilibrated with a 0.03 M tris-HCl buffer solution (pH 7.4), to allow the active substances to adsorb on the column. The adsorbed active substances were washed with 20 liters of a 0.1 M tris-HCl buffer solution containing 0.04 M sodium chloride, then eluted with 20 liters of a 0.1 M tris-HCl buffer solution (pH 7.0) containing 0.15 M sodium chloride and the eluate was dialyzed against distilled water (fraction C).

A calcium phosphate gel was added to the above dialyzed solution in a proportion of 58 ml gel/g protein to allow the active substances to adsorb to the gel. The calcium phosphate gel was collected by filtration, washed twice with 20 liters of a 0.005 M phosphate buffer (pH 6.5), and eluted with 5 liters of a 0.025 M phosphate buffer. The eluate was centrifugated at 12,000×g for 10 minutes to collect the supernatant. The supernatant was dialyzed against distilled water and the dialyzed solution was concentrated to about 50 ml by vacuum evaporation. The concentrate was equilibrated with a 0.1 M tris-HCl buffer, applied to a DEAE-cellulose column (2.5×90 cm) which had been equilibrated with the same buffer, and eluted with a 0.1 M tris-HCl buffer solution containing sodium chloride by the linear chloride concentration gradient elution technique (sodium chloride concentration gradient: 0 to 0.15 M). The fractions containing the glycoprotein were collected and concentrated by means of an ultrafiltration membrane (fraction D).

The concentrate obtained above was subjected to gel filtration using a Biogel P-100 column (2.5×110 cm), which had been equilibrated with a 0.03 M tris-HCl buffer solution, to obtain 230 mg of glycoprotein (standard purity product).

One hundred milligrams of the standard purity product was dissolved in 0.1 M acetate buffer solution (pH 6.0) containing 1.0 M NaCl, 0.001 M $MgCl_2$, 0.001 M $MnCl_2$ and 0.001 M $CaCl_2$, applied to a concanavalin A-Sepharose 4B column (36×1.0 cm) which had been equilibrated with the same buffer solution, and eluted with 0.1 M α-methyl-D-glucoside solution to obtain 8 mg of glycoprotein (highly purified product).

The biological activities on mouse bone marrow cells of various purity grades of glycoprotein were assayed by the aforementioned method. The results were as shown in Table 8.

TABLE 8

| Sample | Specific activity |
| --- | --- |
| Semi-purified product | |
| Fraction A | 21,000 |
| Fraction B | 54,000 |
| Standard purity product | 180,000 |
| Highly purified product | 1,240,000 |

(2) Cultivation of monocytes and macrophages; and purification of CFS in the conditioned medium.

The procedures of Example 1-(3) and 1-(4) were repeated, except that 1,000 units/ml medium of the standard purity glycoprotein was used in place of the highly purified glycoprotein. There were obtained about 5 ml of a purified CSF-containing solution which showed an activity of forming 35,000 human granulocyte colonies per ml of the solution.

EXAMPLE 6

About 5 ml of a purified CSF-containing solution were obtained by repeating the procedure of Example 5, except that a glycoprotein prepared in the following manner by the method of Stanley and Metcalf was used in place of the glycoprotein prepared by the method of Stanley et al. The purified CSF-containing solution obtained in the present Example showed an activity of forming 9,800 human granulocyte colonies per ml of the solution.

Twenty liters of human urine was dialyzed against tap water at room temperature for 8-12 hours. To the dialyzed solution were added 75 g of DEAE-cellulose equilibrated with water and 100 ml of a 1.0 M tris-HCl buffer (pH 7.0). The resulting mixture was thoroughly mixed to allow the glycoprotein to adsorb to the DEAE-cellulose. After removing the supernatant, the DEAC-cellulose was washed three times with 0.1 M tris-HCl buffer (pH 7.0) containing 0.05 M sodium chloride. Thereafter, the adsorbed glycoprotein was eluted with 300 ml of 0.1 M tris-HCl buffer (pH 7.0) containing 0.5 M sodium chloride (this procedure was repeated six times). The eluate was concentrated by vacuum evaporation at 40° C. and dialyzed against 0.1 M tris-HCl buffer (pH 7.0). The dialyzed solution was applied to a DEAE-cellulose column (2.3×44 cm) which had been equilibrated with 0.1 M tris-HCl buffer (pH 7.0) to allow the glycoprotein to adsorb to the DEAE-cellulose. After washing the column with the same buffer containing 0.05 M sodium chloride, the adsorbed glycoprotein was eluted by the sodium chloride concentration gradient elution technique using 0.1–0.5 M sodium chloride in the same buffer. The eluate was dialyzed against water and the dialyzed solution was concentrated by vacuum evaporation and lyophilized. The lyophilized material was dissolved in 0.1 M tris-HCl buffer (pH 7.0) and applied to a Sephadex G-150 column (2.3×150 cm), which had been equilibrated with the same buffer, to collect the glycoprotein fraction. This fraction was dialyzed and lyophilized to obtain about 12 mg of a powder having a specific activity of about 36,000 on mouse bone marrow cells.

EXAMPLE 7

Monocytes and macrophages were separated from the human periphery blood in the same manner as in Example 1. A glycoprotein-containing fraction was prepared in the manner as described below according to the aforementioned method of Laukel et al. and added to serum-free McCoy's 5A medium at a rate of 2,000 units/ml medium. Using this medium, cultivation was carried out in a similar manner to that in Example 5 to obtain 120 ml of a conditioned medium. The conditioned medium was dialyzed against distilled water and the dialyzed solution was concentrated by vacuum evaporation at a low temperature, yielding about 5 ml of a CSF-containing solution which showed an activity of forming 29,000 human granulocyte colonies per ml of the solution, as assayed in the same manner as in Experimental Example 1.

Fifty liters of human urine was dialyzed against running tap water by means of an ultrafiltration membrane apparatus (CL 100 of Asahi Kasei Co.). The dialyzed solution was passed through a DEAE-cellulose column (10×30 cm) which had been equilibrated with 0.05 M tris-HCl buffer (pH 7.3) to allow the glycoprotein to adsorb to the DEAE-cellulose. After washing the column with 0.05 M tris-HCl buffer (pH 7.3) supplemented with 0.05 M sodium chloride, the glycoprotein was eluted with the same buffer supplemented with 0.3 M sodium chloride. The eluate was dialyzed against 0.05 M tris-HCl buffer (pH 8.0) supplemented with 0.5 M NaCl, 2 mM $CaCl_2$ and 2 Mm $MgCl_2$. The dialyzed solution was applied to a concanavalin A-Sepharose 4B column (2.6×40 cm) which had been equilibrated with the same buffer to allow the glycoprotein to adsorb to the column. After washing the column with the same buffer, the glycoprotein was eluted with the same buffer supplemented with 0.15 M α-methyl-D-mannoside. The eluate was concentrated by ultrafiltration to obtain about 7 ml of a fraction containing 6 mg in terms of protein of glycoprotein in 1 ml. The specific activity of this fraction was about 20,000 on mouse bone marrow cells.

EXAMPLE 8

Monocytes and macrophages were separated from the human periphery blood in the same manner as in Example 1. A glycoprotein-containing fraction (fraction D) prepared in the same manner as in Example 5 was added to McCoy's 5A medium supplemented with 10% of human serum at a rate of 2,000 units/ml medium. Using this medium, about 5 ml of a purified CSF-containing solution was obtained in a manner similar to that in Example 5. This solution showed an activity of forming 24,000 human granulocyte colonies per ml of the solution, as assayed in the same manner as in Experimental Example 1.

What is claimed is:

1. A method for producing a substance capable of stimulating the proliferation and differentiation of human granulopoietic stem cells, which comprises cultivating monocytes and macrophages, which have been separated from the human peripheral blood, in a synthetic medium for tissue culture containing a glycoprotein separated from the human urine and capable of stimulating human or mouse bone marrow cells to form human granulocytes or mouse macrophages and granulocytes, thereby producing a substance capable of stimulating the proliferation and differentiation of human granulopoietic stem cells in the medium, and recovering the active substance from the medium.

2. A method according to claim 1, wherein the glycoprotein is a glycoprotein capable of stimulating human bone marrow cells to form human granulocytes.

3. A method according to claim 1, wherein the glycoprotein is a glycoprotein capable of stimulating human bone marrow cells to form mouse macrophages and granulocytes.

4. A method according to claim 1, wherein the cultivation is carried out in the presence of serum.

5. A method according to claim 4, wherein the serum present in the medium is human serum.

6. A method according to claim 5, wherein the amount of the serum is at least 5% based on the volume of the medium.

7. A method according to claim 2, wherein the glycoprotein content of the medium is at least 0.1 µg per ml of the medium.

8. A method according to claim 3, wherein the glycoprotein content of the medium is at least 500 units per ml of the medium.

9. A method for producing a substance capable of stimulating the proliferation and differentiation of human granulopoietic stem cells according to claim 1, wherein the glycoprotein is a partially purified material accompanied with urinary proteins.

10. A method according to claim 1, wherein the number of cells of monocytes and macrophages inoculated into the medium is at least $10^5$ per ml of the medium.

* * * * *